United States Patent [19]
Dinello et al.

[11] Patent Number: 5,522,816
[45] Date of Patent: Jun. 4, 1996

[54] TRANSVERSE CONNECTION FOR SPINAL COLUMN CORRECTIVE DEVICES

[75] Inventors: Alexandre M. Dinello, Shaker Heights, Ohio; Kamal N. Ibrahim, Oakbrook, Ill.; Steven G. Dorsky, Springfield, N.J.

[73] Assignee: AcroMed Corporation, Cleveland, Ohio

[21] Appl. No.: 208,345

[22] Filed: Mar. 9, 1994

[51] Int. Cl.[6] ........................... A61B 17/70; A61B 17/80
[52] U.S. Cl. ................... 606/61; 606/69; 403/400
[58] Field of Search ........................... 606/61, 60, 69, 606/70, 71, 73; 403/3, 384, 388, 362, 199, 142, 398, 400

[56] References Cited

U.S. PATENT DOCUMENTS

| | | | |
|---|---|---|---|
| 5,005,562 | 4/1991 | Cotrel | 606/61 |
| 5,084,049 | 1/1992 | Asher et al. | 606/61 |
| 5,147,360 | 9/1992 | Dubousset | 606/61 |
| 5,334,203 | 8/1994 | Wagner | 606/61 |

FOREIGN PATENT DOCUMENTS

| | | | |
|---|---|---|---|
| 0446092 | 9/1991 | European Pat. Off. | 606/61 |

OTHER PUBLICATIONS

SOCON Internal Fixator User Manual—Oct. 1992.

Primary Examiner—Stephen C. Pellegrino
Assistant Examiner—Scott B. Markow
Attorney, Agent, or Firm—Tarolli, Sundheim, Covell, Tummino & Szabo

[57] ABSTRACT

An apparatus for interconnecting a pair of longitudinal members connectable with vertebrae of a spinal column comprises first and second connector members connectable with the longitudinal members. An elongate plate extends transverse to the longitudinal members and interconnects the first and second connector members. The first connector member includes a hook portion extendable around a portion of the longitudinal member. A set screw clamps the longitudinal member to the hook portion of the connector member. A nut threadably engages the set screw to clamp the elongate plate to the connector member. The elongate plate includes surfaces defining a recess for receiving the connector member. The surfaces defining the recess engage the connector member to prevent the elongate plate from pivoting relative to the connector member.

20 Claims, 2 Drawing Sheets

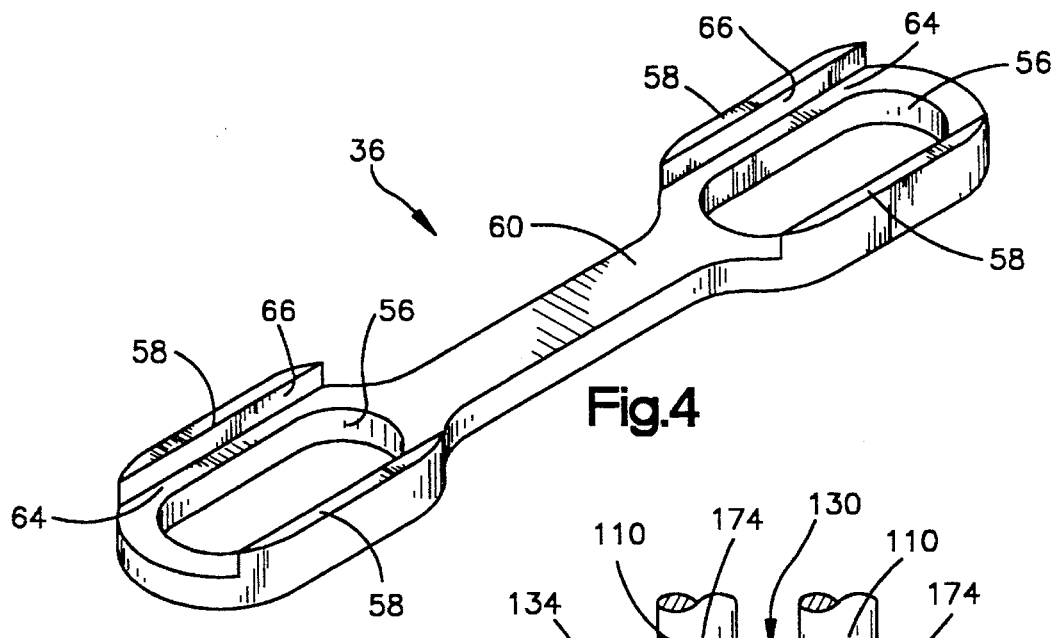
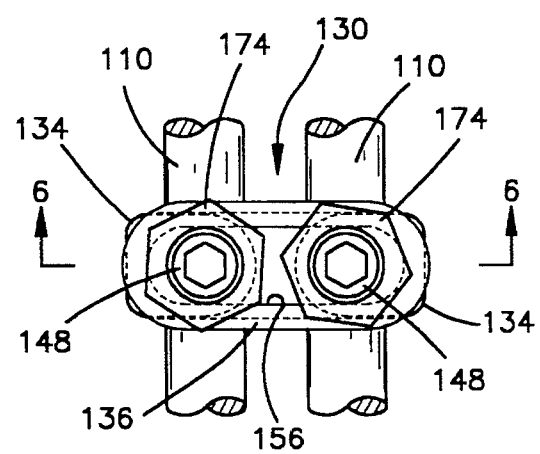
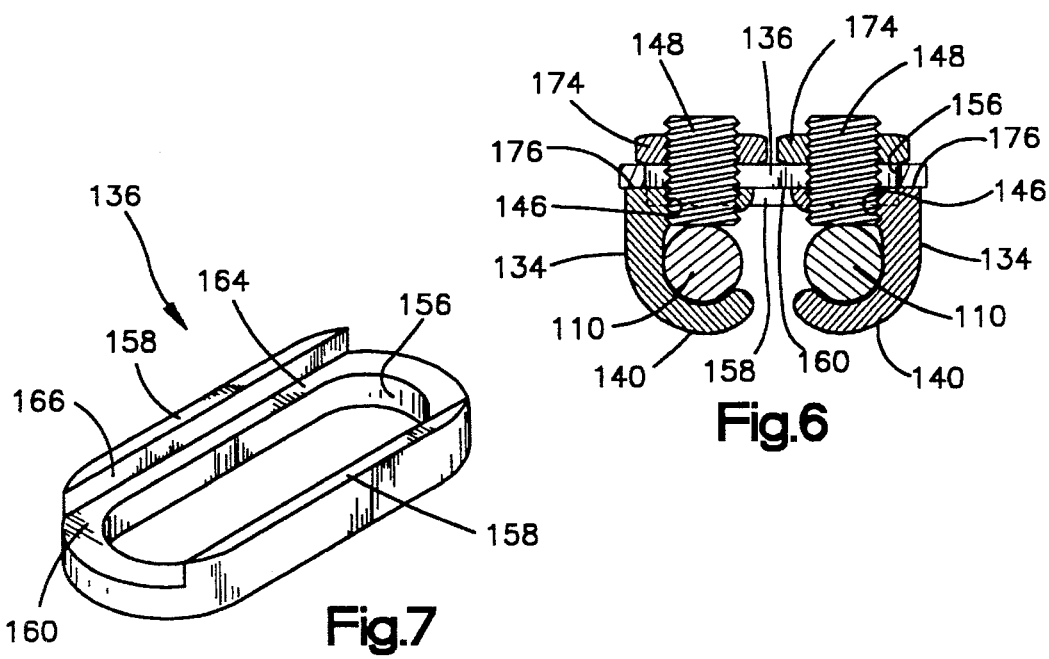

5,522,816

TRANSVERSE CONNECTION FOR SPINAL COLUMN CORRECTIVE DEVICES

BACKGROUND OF THE INVENTION

The present invention relates to transverse connectors for interconnecting longitudinal members of a spinal column corrective device.

Transverse connectors for interconnecting longitudinal members of a spinal column corrective device are known. A known transverse connector includes a pair of eye bolts for receiving parallel longitudinal rods connected to vertebrae of a spinal column. An elongate plate interconnects the eye bolts. The elongate plate includes openings through which threaded portions of the eye bolts extend. Nuts threadably engage the threaded portions of the eye bolts to clamp the longitudinal rods between the eye bolt and the elongate plate.

The eye bolts must be placed on the spinal rods prior to connecting the longitudinal rods to a spinal column. The eye bolts do not hold their positions relative to the longitudinal rods when positioning the elongate plate. The eye bolts and elongate plate must be positioned at the same time, since the nut clamps the eye bolt, elongate plate, and the longitudinal rod together.

SUMMARY OF THE INVENTION

The present invention is directed to a transverse connector for interconnecting a pair of longitudinal members, such as longitudinal rods or plates, which are connectable with vertebrae of a spinal column. The transverse connector includes first and second connector members and an elongate plate extending between the connector members and transverse to the longitudinal rods. The first and second connector members of the transverse connector include hook portions extendable around portions of the longitudinal members. Set screws threadably engage the connector members to clamp the longitudinal members to the hook portions. Nuts threadably engage the set screws to clamp the elongate plate to the connector members.

In one embodiment of the present invention, the set screws extend through first and second oblong openings in the elongate plate to permit adjustment of the position of the elongate plate relative to the connector members. The elongate plate includes surface means defining first and second recesses for receiving the connector members. The surfaces defining the recesses in the elongate plate engage the connector members to prevent pivoting of the elongate plate relative to the connector members.

In another embodiment of the present invention, the elongate plate includes one oblong opening through which both of the set screws extend. The elongate plate has surface means defining a recess for receiving both of the connector members to prevent pivoting of the elongate plate relative to the connector members.

The hook portions allow the transverse connector to be positioned on the longitudinal members after the longitudinal members have been connected to the spinal column. The set screws connect the connector members to the longitudinal members and fix the positions of the connector members relative to the longitudinal members prior to connecting the elongate plate to the connector members. Therefore, the transverse connector of the present invention is easier to use than the known transverse connectors.

BRIEF DESCRIPTION OF THE DRAWINGS

Further features of the present invention will become apparent to those skilled in the art to which the present invention relates from reading the following specification with reference to the accompanying drawings, in which:

FIG. 4 is an enlarged pictorial view of an elongate plate of the transverse connector in FIG. 1;

FIG. 5 is an enlarged plan view of another embodiment of the transverse connector of the present invention interconnecting a pair of spine rods;

FIG. 6 is a cross sectional view of the transverse connector in FIG. 5, taken approximately along the line 6—6 in FIG. 5; and FIG. 7 is an enlarged pictorial view of an elongate plate of the transverse connector in FIG. 5.

DESCRIPTION OF THE PREFERRED EMBODIMENTS

Figure 1:
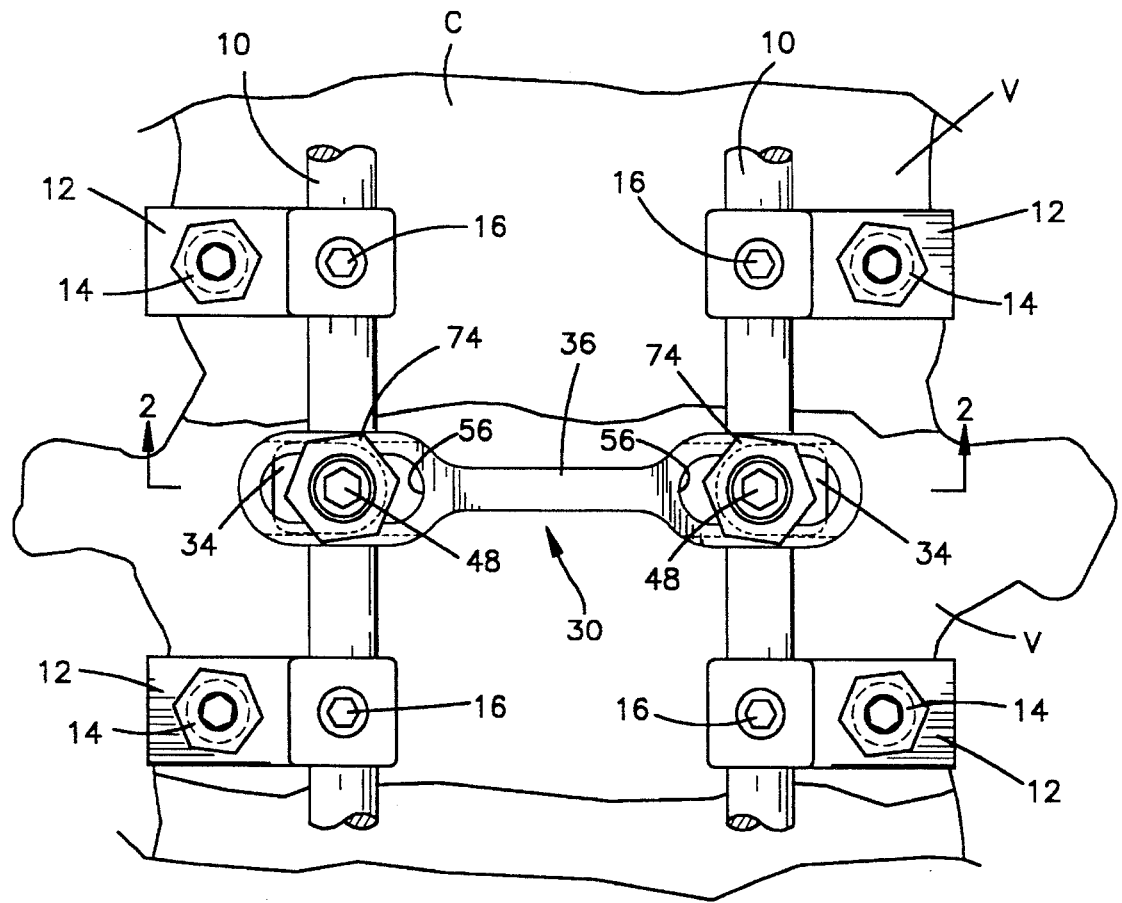
FIG. 1 is an enlarge plan view of one embodiment of the transverse connector of the present invention interconnecting a pair of spine rods which are connected to a spinal column.

One embodiment of the present invention is illustrated in FIGS. 1–4. A portion of a spinal column C (FIG. 1) includes a plurality of vertebrae V. A pair of longitudinal rods 10 are connected to some of the vertebrae V to maintain the relative positions of the vertebrae. It will be apparent that the rods 10 may be located anywhere along spinal column C, and the location of the rods illustrated in FIG. 1 is for example purposes.

Each of the rods 10 is elongate and has a sufficient length to span at least two vertebrae V. A plurality of connectors 12 and fasteners 14 connect the rods 10 with the vertebrae V. The connectors 12 and the fasteners 14 may be of any known construction and are, preferably, the same as those disclosed in U.S. Pat. No. 5,129,900. The connectors 12 include openings through which fasteners 14 extend to connect the connectors to the vertebrae V. The connectors 12 include set screws 16 for clamping the longitudinal rods 10 in openings extending through the connectors.

At least one transverse connector 30 (FIGS. 1 and 2) interconnects the rods 10. The transverse connector 30 blocks relative movement of the rods 10 so the vertebrae V connected to the rods are maintained in their desired relative positions and do not pivot relative to an anterior/posterior axis or a longitudinal central axis of the spinal column C. It will be apparent that the transverse connector 30 may be located anywhere along the rods 10 and that any number of transverse connectors may be used.

The transverse connector 30 includes a pair of identical hook members 34 and an elongate plate 36 extending transverse to the longitudinal rods 10 and interconnecting the hook members. Each of the hook members 34 (FIGS. 2 and 3) includes a hook portion 40 for extending around a portion of the rod 10. The hook portion 40 includes axial spaced arcuate surfaces 42 (FIG. 3) for engaging the rod 10 at axially spaced locations. Reference is hereby made to U.S. Pat. No. 5,024,213 to Asher et al. and assigned to the same assignee as the present invention. U.S. Pat. No. 5,024,213 describes the arcuate surfaces and their function in greater detail.

Figure 2:
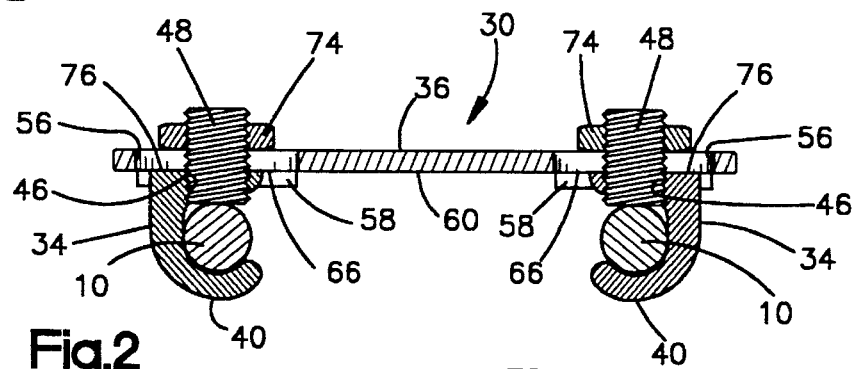
FIG. 2 is a cross sectional view of the transverse connector in FIG. 1, taken approximately along the line 2—2 in FIG. 1.
Figure 3:
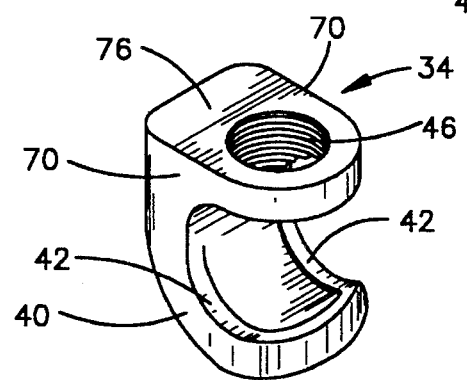
FIG. 3 is an enlarged pictorial view of a hook member of the transverse connector in FIG. 1.

The hook member 34 includes a threaded opening 46 for receiving a set screw 48 (FIG. 2). The set screw 48 engages the rod 10 to clamp the rod against the arcuate surfaces 42 of the hook portion 40. The elongate plate 36 includes a pair of oblong openings 56 (FIGS. 2 and 4) through which the set screws 48 extend. The oblong openings 56 permit adjustment of the position of the elongate plate 36 relative to the hook members 34. Four lip portions 58 (FIG. 4) extend from a surface 60 of the elongate plate. The lip portions 58 extend on opposite sides of the oblong openings 56 and parallel to the longitudinal axes of the oblong openings.

The lip portions 58 define recesses 64 in the elongate plate 36 for receiving the hook members 34. Inner side surfaces 66 (FIG. 4) of the lip portions 58 engage side surfaces 70 (FIG. 3) of the hook members 34 to prevent pivoting of the elongate plate 36 relative to the hook members. Nuts 74 (FIG. 2) threadably engage the set screws 48 and engage the plate 36 to clamp the elongate plate to the hook members 34. The nuts 74 engages surfaces on opposite sides of the oblong openings 56 to clamp the surface 60 of the elongate plate against upper surfaces 76 of the hook members 34.

The longitudinal rods 10 are connected to the vertebrae V by the fasteners 14 and connectors 16. The hook members 34 are then connected to the rods 10 by the set screws 48. The elongate plate 36 is placed over the hook members 34 with the hook members in the recesses 64 and the set screws 48 extending through the oblong openings 56. The position of the plate 36 is adjusted by sliding the plate relative to the hook members 34 along the longitudinal axis of the plate. The nuts 74 are threaded onto the set screws 48 to clamp the plate 36 to the hook members 34.

Although the elongate plate 36 has been described as having two oblong openings 56, it is contemplated that the plate could have one oblong opening and one round opening for receiving a set screw 48. The position of the plate 36 would not be adjustable relative to one of the hook members 34.

Another embodiment of the transverse connector of the present invention is illustrated in FIGS. 5–7. Longitudinal rods 110 are connected to vertebrae (not shown) by connectors and fasteners (not shown) as described in connection with the embodiment of FIG. 1. At least one transverse connector 130 (FIGS. 5 and 6) interconnects the longitudinal rods 110 to block relative movement between the rods. The transverse connector 130 includes a pair of identical hook members 134 and an elongate plate 136.

The hook members 134 (FIG. 6) are identical to the hook members 34 described in connection with the embodiment of FIGS. 1–4 and, therefore, will not be described in detail. Each hook member 134 includes a hook portion 140 extendable around a portion of the rod 110. Axially spaced arcuate surfaces (not shown) on the hook portion 140 engage the rods 110 at axially spaced locations. The hook member 134 includes a threaded opening 146 for receiving a set screw 148 which clamps the rod 110 to the hook portion 140.

The elongate plate 136 includes an oblong opening 156 (FIGS. 6 and 7) through which the set screws 148 extend. The oblong opening 156 permits adjustment of the position of the elongate plate 136 relative to the hook members 134. The plate 136 includes a pair of lip portions 158 (FIG. 7) extending from a surface 160 of the plate. The lip portions 158 extend on opposite sides of the oblong opening 156 and parallel to the longitudinal axis of the oblong opening. The lip portions 158 define a recess 164 for receiving the hook members 134.

The lip portions 158 include inner side surfaces 166 for engaging the hook members 134 to prevent relative pivoting between the plate 136 and the hook members. Nuts 174 (FIG. 6) threadably engage the set screws 148 to clamp the elongate plate 136 to the hook members 134. The nuts 174 engage surfaces adjacent the elongate opening 156 to clamp the surface 160 of the plate to upper surfaces 176 of the hook members 134.

The longitudinal rods 110 are connected to the vertebrae V by fasteners and connectors as described in connection with the embodiment of FIGS. 1–4. The hook members 134 are then connected to the rods 110 by the set screws 148. The plate 136 is placed over the hook members 134 with the hook members in the recess 164 and the set screws 148 extending through the oblong opening 156. The position of the plate 136 is adjusted by sliding the plate relative to the hook members 134 along the longitudinal axis of the plate. The nuts 134 are threaded onto the set screws 148 to clamp the plate 136 to the hook members 134.

Although the present invention has been shown interconnecting a pair of longitudinal rods, it is contemplated that the transverse connectors of the present invention could be used to interconnect a pair of longitudinal plates. It is also contemplated that the elongate plates of the present invention may not include lip portions for engaging the hook members.

From the above description of the invention, those skilled in the art will perceive improvements, changes and modifications. Such improvements, changes and modifications within the skill of the art are intended to be covered by the appended claims.

Having described the invention, the following is claimed:

1. An apparatus for interconnecting a pair of longitudinal members extending substantially parallel to each other and connectable with vertebrae of a spinal column, said apparatus comprising:

a first connector member connectable with one of the longitudinal members, said first connector member including a hook portion extendable around a portion of the one longitudinal member;

first means for releasably connecting the one longitudinal member to said hook portion of said first connector member, said first connecting means comprising a set screw threadably engaging said first connector member, said set screw being engageable with the one longitudinal member to clamp the one longitudinal member to said hook portion;

a second connector member connectable with the other longitudinal member;

means for interconnecting said first and second connector members extending between said first and second connector members and transverse to the longitudinal members; and second means for releasably connecting said interconnecting means to said first connector member after said first connecting means has connected said hook portion to the one longitudinal member, said second connecting means comprising a nut threadably engaging said set screw, said nut engaging said interconnecting means to clamp said interconnecting means to said first connector member.

2. An apparatus as set forth in claim 1 wherein said interconnecting means comprises an elongate plate having an opening, said set screw extending through the opening in said elongate plate.

3. An apparatus as set forth in claim 2 wherein the opening in said elongate plate is oblong to permit adjustment of the relative positions of said elongate plate and said first connecting member.

4. An apparatus for interconnecting a pair of longitudinal members extending substantially parallel to each other and connectable with vertebrae of a spinal column, said apparatus comprising:

a first connector member connectable with one of the longitudinal members, said first connector member including a hook portion extendable around a portion of the one longitudinal member;

first means for releasably connecting the one longitudinal member to said hook portion of said first connector member;

a second connector member connectable with the other longitudinal member, said second connector member including a hook portion extendable around a portion of the other longitudinal member;

means for interconnecting said first and second connector members extending between said first and second connector members and transverse to the longitudinal members;

second means for releasably connecting said interconnecting means to said first connector member after said first connecting means has connected said hook portion to the one longitudinal member;

third connecting means for releasably connecting the other longitudinal member to said hook portion of said second connector member, said third connecting means comprising a set screw threadably engaging said second connector member and engageable with the other longitudinal member to clamp the other longitudinal member to said second connector member; and fourth connecting means for connecting said interconnecting means to said second connector member, said fourth connecting means comprising a nut threadably engaging said set screw and engaging said interconnecting means to clamp said interconnecting means to said second connector member.

5. An apparatus for interconnecting a pair of longitudinal members extending substantially parallel to each other and connectable with vertebrae of a spinal column, said apparatus comprising:

a first connector member connectable with one of the longitudinal members, said first connector member including a hook portion extendable around a portion of the one longitudinal member;

first means for releasably connecting the one longitudinal member to said hook portion of said first connector member;

a second connector member connectable with the other longitudinal member;

means for interconnecting said first and second connector members extending between said first and second connector members and transverse to the longitudinal members, said interconnecting means comprising an elongate plate extending between said first and second connector members; and second means for releasably connecting said interconnecting means to said first connector member after said first connecting means has connected said hook portion to the one longitudinal member.

6. An apparatus as set forth in claim 5 wherein said elongate plate includes means for engaging said first connector member to prevent pivoting of said elongate plate relative to said first connector member.

7. An apparatus as set forth in claim 6 wherein said means for engaging said first connector member includes surface means defining a first recess for receiving said first connector member, said surface means engaging said first connector member to prevent pivoting of said elongate plate relative to said first connector member.

8. An apparatus as set forth in claim 7 wherein said second connector member is received in the first recess, said surface means engaging said second connector member to prevent pivoting of said elongate plate relative to said second connector member.

9. An apparatus as set forth in claim 1 wherein said elongate plate includes surface means defining a second recess for receiving said second connector member, said surface means defining the second recess engaging said second connector member to prevent pivoting of said elongate plate relative to said second connector member.

10. An apparatus as set forth in claim 5 wherein said elongate plate includes a first oblong opening, said first connecting means extending through the first oblong opening.

11. An apparatus as set forth in claim 10 further including means for connecting said second connector member to the other longitudinal member extending through the first oblong opening in said elongate plate.

12. An apparatus as set forth in claim 10 further including means for connecting said second connector member to the other longitudinal member, said elongate plate including a second oblong opening, said means for connecting said second connector member to the other longitudinal member extending through the second oblong opening.

13. An apparatus for interconnecting a pair of longitudinal members extending substantially parallel to each other and connectable with vertebrae of a spinal column, said apparatus comprising:

a member extendable transverse to the longitudinal members; and first and second connector means for connecting said member to the longitudinal members;

said member including first and second portions extending from a surface of said member, said surface of said member defining a bottom of a recess for receiving said first connector means, said first and second portions having surface means defining sides of the recess for receiving said first connector means, said first connector means engaging said surface of said member and said surface means defining said sides of the recess to prevent pivoting of said member relative to said first connector means.

14. An apparatus as set forth in claim 13 wherein the recess in said member receives said second connector means, said surface means defining the recess engaging said second connector means to prevent pivoting of said member relative to said second connector means.

15. An apparatus as set forth in claim 14 wherein said member includes an oblong opening, each of said first and second connector means including a portion extending into the oblong opening.

16. An apparatus as set forth in claim 15 wherein each of said first and second connector means includes a hook portion, a set screw, and a nut, said set screws being engageable with the longitudinal members to clamp the longitudinal members to said hook portions, said set screws extending through the oblong opening in said member, said nuts threadably engaging said set screws to clamp said member to said hook portions.

17. An apparatus as set forth in claim 13 wherein said member includes a first oblong opening through which a portion of said first connector means extends.

18. An apparatus as set forth in claim 17 wherein said member includes third and fourth portions extending from said surface of said member having surface means defining a second recess for receiving said second connector means, said second connector means engaging said surface means defining the second recess to prevent pivoting of said member relative to said second connector means.

19. An apparatus as set forth in claim 18 wherein said member includes a second oblong opening through which a portion of said second connector means is extendable.

20. An apparatus as set forth in claim 19 wherein each of said first and second connector means includes a hook portion, a set screw, and a nut, said set screws being engageable with the longitudinal members to clamp the longitudinal members to said hook portions, said set screws extending through the respective oblong openings in said member, said nuts threadably engaging said set screws to clamp said member to said hook portions.

* * * * *

UNITED STATES PATENT AND TRADEMARK OFFICE
CERTIFICATE OF CORRECTION

PATENT NO.  : 5,522,816
DATED       : June 4, 1996
INVENTOR(S) : Alexandre M. Dinello, Kamal N. Ibrahim and Steven G. Dorsky It is certified that error appears in the above-indentified patent and that said Letters Patent is hereby corrected as shown below:

Column 6, line 15, change "1" to --7--.

Signed and Sealed this

Twenty-fourth Day of September, 1996

Attest:

BRUCE LEHMAN

*Attesting Officer*   *Commissioner of Patents and Trademarks*